United States Patent [19]

Takeo et al.

[11] Patent Number: 4,762,825

[45] Date of Patent: Aug. 9, 1988

[54] POLYSACCHARIDE RON SUBSTANCE

[75] Inventors: Suguru Takeo; Hisao Yamamoto; Hisao Kado; Nobuhiro Watanabe; Minoru Kamimura, all of Yaizu; Kiichi Uchida, Fujisawa; Yoshitada Mori, Tokyo, all of Japan

[73] Assignees: Sapporo Breweries Limited, Tokyo; Daicel Chemical Industries, Ltd., Sakai; Etsuo Ito, Urasoe, all of Japan

[21] Appl. No.: 765,007

[22] Filed: Aug. 12, 1985

[30] Foreign Application Priority Data

Aug. 22, 1984 [JP] Japan .................................. 59-173168

[51] Int. Cl.$^4$ ........................ A61K 31/73; C08B 37/00
[52] U.S. Cl. ....................................... 514/54; 514/23; 536/1.1; 536/55.1; 536/128; 435/72

[58] Field of Search .................. 536/1.1, 55.1; 514/54, 514/23

[56]  References Cited

U.S. PATENT DOCUMENTS 4,357,323 11/1982 Soma et al. .......................... 536/128
4,366,308 12/1982 Soma et al. .......................... 536/1.1

Primary Examiner—Ronald W. Griffin
Assistant Examiner—Elli Peselev
Attorney, Agent, or Firm—Frishauf, Holtz, Goodman & Woodward

[57] ABSTRACT

A polysaccharide RON substance having the ultraviolet absorption spectrum depicted in FIG. 1, the infrared absorption spectrum depicted in FIG. 2 and the $^{13}$C-NMR spectrum depicted in FIG. 3 is obtained from rice bran by extraction and purification; and pharmacological composition containing said RON substance.

2 Claims, 3 Drawing Sheets

4,762,825

POLYSACCHARIDE RON SUBSTANCE

BACKGROUND OF THE INVENTION

1. Field of the Invention

This invention relates to a novel polysaccharide RON substance and antitumor agent, immunomodulating agent, host defense agent against infectious disease, and inducer of tumor necrosis factor containing said substance as the effective component.

2. Description of the Prior Art

As is known in the art, polysaccharides are obtained from various sources, for example, Basidiomycetes (Japanese Patent Kokai Koho No. 94012/1978), bacteria (Japanese Patent Kokai Koho No. 76896/1979), mould (Japanese Patent Publication No. 59097/1978), algae (Japanese Patent Kokai Koho No. 28923/1977), and grains (Japanese Patent Kokai Koho No. 139713/1978).

It is also known that these polysaccharides have antitumor activity. However, various problems, for example, low yields, complicated production process, toxicity, etc., are encountered in using such polysaccharides as an antitumor agent.

SUMMARY OF THE INVENTION

According to the present invention, it has been found that a novel polysaccharide RON substance can be obtained from rice bran, and that the polysaccharide RON substance is effective as an antitumor agent against transplantable tumors, an immunomodulating agent, a host defense agent against infectious disease, and an inducer of tumor necrosis factor.

The present invention relates to:

(1) a novel polysaccharide RON substance;

(2) a process for producing the polysaccharide RON substance which comprises the steps of:

treating a rice bran with hot water to extract said polysaccharide RON substance into the water, adding a polar organic solvent or a salting-out agent to the water containing the extracted substance to form precipitates containing said polysaccharide RON substance, isolating the precipitates (3) a pharmaceutical composition effective in inhibiting the growth of tumors of mice containing the polysaccharide RON substance as an effective ingredient;

(4) a pharmaceutical composition effective in modulating the immunological state of mice containing the polysaccharide RON substance as an effective ingredient;

(5) a pharmaceutical composition effective in potentiating the host defense ability against infectious microorganisms containing the polysaccharide RON substance as an effective ingredient; and (6) a pharmaceutical composition effective in inducing the production of tumor necrosis factor in mice containing the polysaccharide RON substance as an effective ingredient.

DETAILED DESCRIPTION OF THE INVENTION

Figure 1:
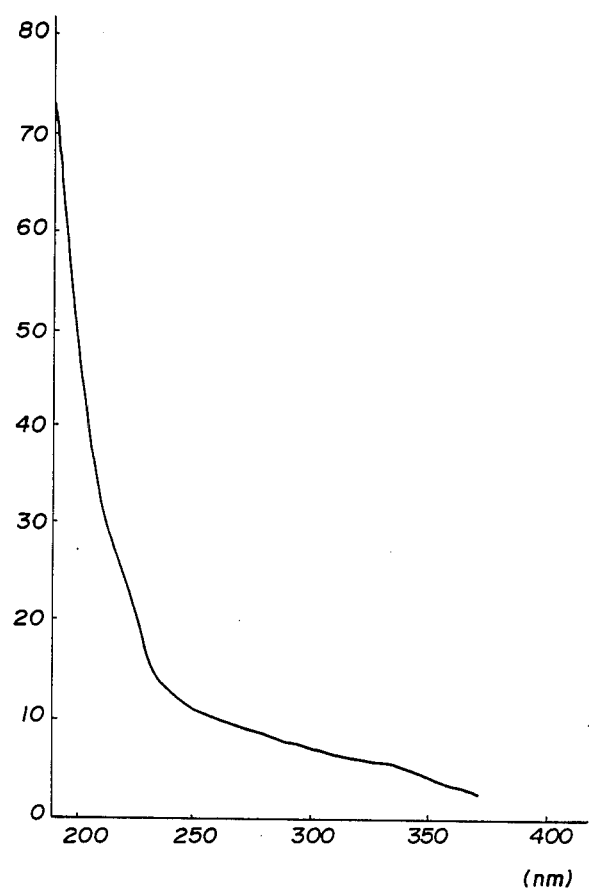
FIG. 1 is an ultraviolet absorption spectrum of the polysaccharide RON substance produced by the process of the present invention.

This invention relates to a novel polysaccharide RON substance, a process for the production of said substance, and antitumor agent against transplantable tumors, immunomodulating agent, host defense agent against infectious microorganisms, and inducer of tumor necrosis factor in mice containing said substance as the effective component.

The polysaccharide RON substance of this invention is obtained from rice bran by extraction and purification. This rice bran is a by-product obtained in the production of polished rice from unpolished rice, and it is not limited by the variety of the unpolished rice, the producing district, the degree of polishing rate, etc. Prior to the extraction and purification of the polysaccharide RON substance from the rice bran, it is desirable to fully wash the rice bran in order to eliminate the pulverized (or crushed) rice and other impurities. Those rice brans which have already been used for other purposes, such for example as defatted rice bran, which is a residue after extraction of rice-bran oil from rice bran, can be used in this invention.

The polysaccharide RON substance of this invention is produced by adding organic solvents or salting-out agents to an extract obtained by hot water treatment of rice bran to provide precipitates and, if desired, dissolving the obtained precipitates in water to purify them.

The rice bran is passed through a separator, for example, a screen, to remove impurities and is washed with water, if necessary, after pulverization. It is desirable to remove a lipid soluble fraction using organic solvents, such as ethyl acetate, carbon tetrachloride, chloroform, ether, n-hexane, benzene, petroleum ether, acetone etc.

The hot water treatment of the rice bran is carried out by feeding rice bran and distilled or purified water in amount of about 2–100 times, preferably about 5–10 times to that of the rice bran to a vessel with or without stirring under the conditions of pressure of from 0 to 90 kg/cm$^2$, preferably from 0 to 5.0 kg/cm$^2$ and a temperature of from 50° C. to 300° C., preferably from 100° C. to 150° C. for 10 minutes to 24 hours, preferably 0.5 to 5 hours. Practically it is suitable to carry out the hot water treatment at a pressure of from 0 to 3.0 kg/cm$^2$ and a temperature of from 100° C. to 140° C. for 1 to 5 hours.

The extract obtained by the hot water treatment is subjected to operations such as filtration, centrifugation, etc. to separate solids and, if necessary, is then concentrated to an appropriate volume by applying such means as concentration at a reduced pressure, ultrafiltration, etc., singly or in combination with each other.

By collecting precipitates formed by adding a water-soluble polar organic solvent or a salting-out agent to the extract, a crude polysaccharide RON substance is obtained.

Polar organic solvents which can be used in this procedure include methanol, ethanol, propanol, acetone, etc. The amount of the polar organic solvent being used is determined taking into account the amount of the desired substance contained in the extract, etc. For example, in the case of ethanol, it may be added in such a manner that the ethanol concentration is 30 to 50%

(v/v). The formed precipitates are preferably washed with the organic solvent as described above, for example, ethanol, etc.

Salting-out agents which can be used in the above procedure include sodium chloride, ammonium sulfate, and potassium chloride. The salting-out agent is usually added until the degree of saturation reaches 0.5 to 1 to thereby form precipitates.

The deproteinization and purification of the polysaccharide RON substance can be carried out either prior to the addition of the organic solvent or salting-out agent to the extract or after the formation of precipitates by the addition of the organic solvent or salting-out agent followed by dissolving the precipitates in water.

For the purification and deproteinization treatment, various known procedures can be applied. For example, amylolytic enzyme and/or proteolytic enzyme is added to a solution containing the polysaccharide RON substance to convert impurities existing therein, such as starch, protein, etc., into low molecular weight compounds. These low molecular weight compounds are removed at a subsequent purification step.

As such enzymes, an amylolytic enzyme, for example α-amylase, a proteolytic enzyme, for example pronase, and if necessary, other enzymes can be used. In this enzyme treatment, it is preferred that the enzyme is added in a ratio of from 1/1000 to 1/5000 of the substrate and that the treatment is carried out for 0.5 to 24 hours, preferably 1 to 15 hours.

Additionally, the following purification and deproteinization methods can be used: a method in which an inorganic or organic acid, such as hydrochloric acid, tannic acid, trichloroacetic acid, etc. is added to an aqueous solution containing the above-described polysaccharide RON substance in a proportion of about 0.1 to 10 wt. %, preferably about 3 to 5 wt. %. When precipitates are formed, they are removed by such operations as filtration, cetrifugation, etc. and subsequently the remaining acids, inorganic ions and low molecular fractions are dialyzed for 1 to 3 days against a running water or a distilled water using a dialysis membrane; an ion exchange method in which a cation or anion exchanger, is used; an ultrafiltration method in which a membrane having an exclusion molecular weight of 10,000 to 100,000 is used; gel filtration; centrifugation; treatment with active carbon; concentration and a combination thereof. The Sevag's method is also applicable for deproteinization. Furthermore the RON substance can be treated by using acids and/or some enzymes to lower the molecular weight thereof.

These purification methods can be applied singly or in combination with each other, and such combinations and the order in which they are applied are subject to no limitations.

When an aqueous solution of high molecular polysaccharide RON substance which has been purified by the above-described methods was applied on such an anion exchanger column as Amberlite IR-4B, DEAE-Sepharose, or DEAE-Cellulose, the fractions passed through the column was collected. From these fractions, a white powder polysaccharide RON substance can be obtained either by lyophilization, spray-drying, or precipitation with a polar organic solvent.

The thus obtained polysaccharide RON substance has the following physical and chemical properties:

This substance has as a structural repetition unit $(6\ G)$ wherein G is α-D-glucopyranosyl group, and does not pass through a dialysis membrane (thus, the molecular weight of this substance may be about 10,000 or more) and is insoluble in organic solvents, for example, alcohols such as methanol, ethanol, propanol, butanol, etc., acetone, hexane, benzene, ethylacetate, ligroin, carbon tetrachloride, chloroform, and ethers, but is soluble in water, dimethylsulfoxide and formamide; A 1% aqueous solution of the present substance is neutral.

The present substance has no melting point and it turns brown at 220° C. and black at 280° C. (carbonizing); Elementary analysis shows that the present substance obtained in Example 1 as described later comprises 40.4–42.4% of carbon, 5.8–6.4% of hydrogen and 3.1–3.3% of ash.

A 1% aqueous solution of the present substance is positive in the following color reactions: phenol-sulfuric acid reaction, anthrone-sulfuric acid reaction and chromotrope-sulfuric acid reaction, and negative in the following color reaction: biuret reaction, the Lowry-Folin reaction, the Elson-Morgan reaction, and starch-iodine reaction;

The specific rotation of the present substance is $[\alpha]_D^{20} = +142°$ to $+145°$ (H$_2$O);

The ash component comprises Si, P, K, Na, Ca, Mg, Cl, etc. When the RON substance is applied on a gel filtration with Sepharose CL-6B (Pharmacia Chemicals AB), these elements and polysaccharide component of the substance are co-eluted in a void volume.

Therefore it is assumed that the above elements do not exist independently as a contaminant in the RON substance, but they exist in the state that they are bound chemically to a skeleton of the RON substance.

The supernatant liquid obtained by a method which comprises hydrolyzing the RONsubstance with 1N sulfuric acid, at 100° C. for 3 hours and then adding barium carbonate to neutralize, is positive in the following color reactions: the Molisch reaction, anthrone-sulfuric acid reaction, tryptophane-sulfuric acid reaction, cystein-sulfuric acid reaction, chromotrope-sulfuric acid reaction, and negative in the following color reactions: biuret reaction, ninhydrin reaction, the Lowry-Folin reaction;

On developing with the four solvents as noted below in the thin layer chromatographic analysis of those products obtained by complete hydrolysis of the RON substance with formic acid and sulfuric acid, no spots except for the one identified as glucose could be detected.

(1) ethyl acetate methanol:acetic acid:water (65:15:10:10)

(2) ethyl acetate:isopropanol:water (65:23:12)

(3) isopropanol:pyridine:water:acetic acid (8:8:4:1)

(4) n-butanol:pyridine:water (6:4:3)

Thus it can be concluded that the present RON substance is a polysaccharide consisting essentially of glucose as a sole sugar component.

Figure 2:
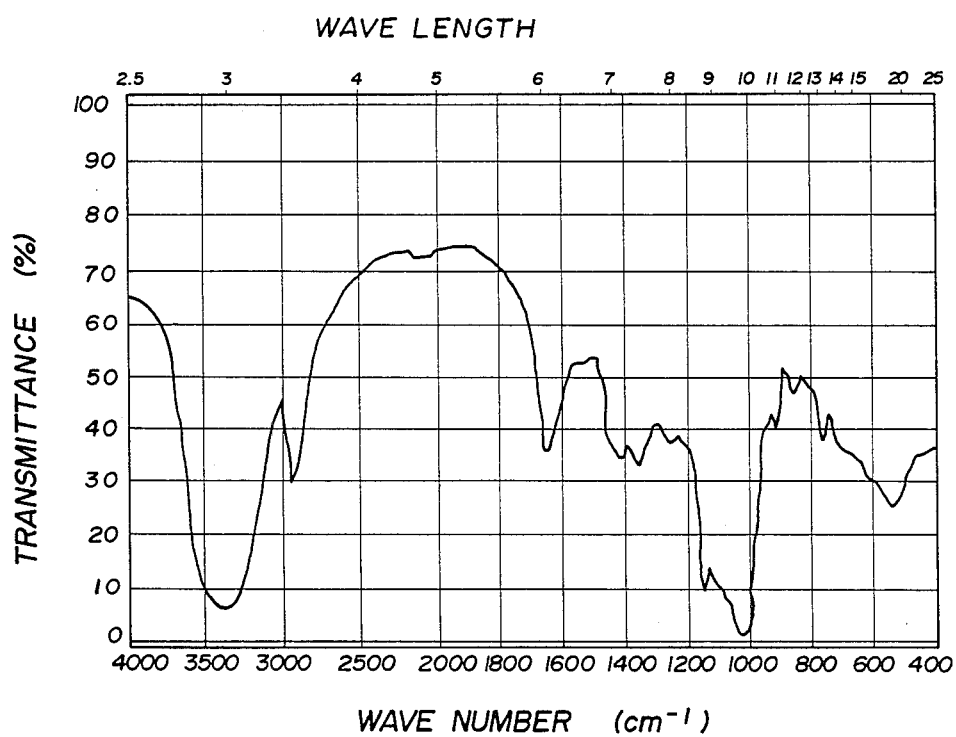
FIG. 2 is an infrared absorption spectrum of said polysaccharide RON substance.
Figure 3:
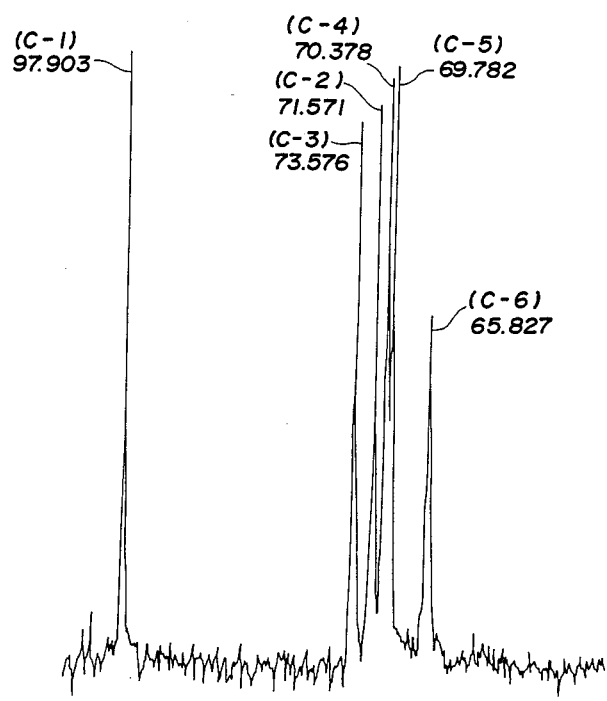
FIG. 3 is a $^{13}$C-NMR spectrum of said polysaccharide RON substance.

The present RON substance has an ultraviolet absorption spectrum as shown in FIG. 1, an infrared absorption spectrum as shown in FIG. 2, and a $^{13}$C-NMR spectrum as shown in FIG. 3. From these spectra and specific rotation, it is assumed that the α-bond exists in the RON substance.

Based upon the above described data, it is assumed that the RON substance of this invention is a polysaccharide comprising glucose as a sole sugar component.

Moreover, on periodate oxidation, the present RON substance consumed 1.95 mole of sodium periodate and released 0.97 mole of formic acid per glucose residue.

The Smith-degradation of this substance gave a lot of glycerine detected by paper chromatographic analysis. Methylation analysis of this substance yielded only 2,3,4-tri-O-methyl-D-glucose.

Based upon the above-described data, it is assumed that the RON substance of this invention is a polysaccharide which is composed solely of linear α-1,6-glucoside linkage. This structure was also confirmed by the analytical data of $^{13}$C-NMR.

It has been made clear that the polysaccharide RON substance of this invention has various biological activities such as antitumor against transplantable tumors, immunomodulating, host defence activities against infectious microorganisms and inducing activities of tumor necrosis factor in mice. The methods and results of testing these biological activities of the polysaccharide RON substance produced in the Example 1 will be described in detail.

(1) Antitumor Activities (a) Effect Of Intraperitoneal Administration of the RON Substance Against a Syngeneic Tumor Meth-A Fifty 6-week-old female BALB/C-CRJ mice (average weight, 20 grams (g)) were transplanted with Meth-A tumor cells ($1 \times 10^5$ cells/mouse) intraperitoneally, which had been grown for one week intraperitoneally in the mouse of the same strain. These mice were divided into four groups; a group of 20 mice as a control group and three groups of 10 mice each as test groups. For 5 consecutive days from the day after the transplantation of the tumor cells, the RON substance dissolved in a saline was administered intraperitoneally in a dose of 10, 30 or 100 milligrams per kilogram (mg/kg) for the test groups. For the control group, on the other hand, only a saline was administered in the same manner. The survival time (days) was measured and the prolongation of life was calculated by the following equation:

$$\text{Prolongation of life (\%)} = \frac{\text{Average survival time (days) for test group}}{\text{Average survival time (days) for control group}} \times 100$$

(b) Effect of Oral Administration of the RON Substance Against a Syngeneic Tumor Meth-A Fifty 6-week-old female BALB/C-CRJ mice (average weight, 20 g) were transplanted with Meth-A tumor cells ($1 \times 10^4$ cells/mouse) subcutaneously in the axillary region, which had been grown for one week intraperitoneally in the mouse of the same strain. These mice were divided into four groups; a group of 20 mice as a control group and three groups of 10 mice each as test groups. For 10 consecutive days from the day after the transplantation of the tumor cells, the RON substance dissolved in a saline was administered orally in a dose of 10, 30 or 100 mg/kg, for the test groups. For the control group, on the other hand, only a saline was administered in the same manner. Thirty five days after the transplantation of the tumor cells, the mice were killed and the tumor developed was cut away and weighed. The inhibition ratio was calculated by the following equation:

$$\text{Inhibition ratio (\%)} = \left(1 - \frac{\text{Average weight of tumor for test groups}}{\text{Average weight of tumor for control group}}\right) \times 100$$

The antitumor activities of the RON substance as assayed by the above-described methods (a) and (b) are shown in the Table I.

TABLE I

| Sample | Dose (mg/kg) | Intraperitoneal Administration (a) | | Oral Administration (b) | |
|---|---|---|---|---|---|
| | | Average Survival Time (days) | Prolongation of Life (%) | Average Tumor Weight (g) | Inhibition Ratio (%) |
| Control (Saline) | — | 20.8 | — | 10.20 | — |
| RON Substance | 10 | 31.2 | 150 | 6.12 | 40 |
| | 30 | >42.0 | >200 | 4.08 | 60 |
| | 100 | 34.3 | 165 | 4.59 | 45 |

From the results shown in the Table I, it can be seen that the RON substance exhibits a strong antitumor activity against a tumor of mice with the optimum dose of about 30 mg/kg both by intraperitoneal and by oral administration.

In addition, it has been confirmed using mice that the RON substance was also effective against Lewis lung carcinoma, Melanoma B-16, Sarcoma-180, and Ehrlich ascites carcinoma, within a dose range of from 10 to 100 mg/kg by intraperitoneal or oral administration with the results that the tumor inhibition ratio was from 30 to 70%. Furthermore, the RON substance is of no toxicity as described hereinafter. Thus the RON substance is believed to find use as a very effective antitumor agent.

(2) Immunomodulating Activities (a) Carbon Clearance Test (CCT)

This test is used to examine the effect of a substance to enhance the phagocytic activity of macrophage amongst the immunomodulating actions.

The RON substance dissolved in a saline was administered intraperitoneally to a test group of six 4-week-old female ICR-CRJ mice (average weight, 20 g) for 2 days. On the other hand, only a saline was administered for the control group in the same manner. At the third day, 0.25 ml of a carbon solution (prepared by diluting a black ink—Found India manufactured by Perikan Co.—with a saline to 5 times) was injected into the tail vein. Just after the injection and also 10 minutes after the injection, 0.025 ml of blood was collected from the venous plexus of the retro-orbit of the mice, suspended in 3.5 ml of a 0.01 M sodium carbonate solution, and the absorbance (OD$_{650}$) at 650 nm was measured to determine a rate of decrease in the concentration of the carbon in the blood. This is indicated by a phagocytic index as defined by the following equation:

$$\text{Phagocytic index } (K) = \frac{\log C_1 - \log C_2}{T_2 - T_1}$$

where $C_1$ is an absorbance (OD$_{650}$) at the time $T_1$ and $C_2$ is that at the time $T_2$.

With regard to tumor-bearing mice, Sarcoma-180 cells were transplanted in the muscle of the hind leg of the mice ($1 \times 10^7$ cells/mouse) 7 days before the start of administration of the RON substance and, thereafter, the mice were tested in the same manner as above. The results are shown in the Table II.

TABLE II

| Sample | Dose (mg/kg) | Normal Mice Phagocytic Index | Normal Mice Relative Value (%) | Tumor-bearing Mice Phagocytic Index | Tumor-bearing Mice Relative Value (%) |
|---|---|---|---|---|---|
| Control (Saline) | — | $40.9 \times 10^{-3}$ | 100 | $110 \times 10^{-3}$ | 100 |
| RON Substance | 10 | 53.6 | 135 | 126 | 115 |
| | 30 | 92.0 | 225 | 164 | 155 |
| | 100 | 81.8 | 200 | 145 | 132 |

It can be seen from the results shown in the Table II that for both of the normal and the tumor-bearing mice the administration of the RON substance in an amount of from 10 to 100 mg/kg, particularly in 30 mg/kg enhanced the function of the reticuloendothelial system of the mice and greatly intensified the phagocytic activity of macrophage.

(b) Plaque-forming Cell Test (PFC)

This method is used to examine the effect of a substance to enhance the antibody-producing ability due to the activation of B cells of the host amongst the immunomodulating actions.

The RON substance dissolved in a saline was administered intraperitoneally to a test group of six 4-week-old female ICR-CRJ mice (average weight, 20 g) for 3 consecutive days. For the control group, only a saline was administered in the same manner. At the fourth day and also at the eleventh day, sheep red blood cells were injected into the tail vein ($4 \times 10^8$ cells/mouse) to sensitize the mice. Four days after the injection, the plaque-forming ability of the spleen cells of mice was determined by the method of Cunningham. The results are shown in the Table III.

TABLE III

| Sample | Dose (mg/kg) | Sensitization on 4th day Number of Plaques per Spleen | Sensitization on 4th day Relative Value (%) | Sensitization on 11th day Number of Plaques per Spleen | Sensitization on 11th day Relative Value (%) |
|---|---|---|---|---|---|
| Control (Saline) | — | $3.0 \times 10^4$ | 100 | $2.6 \times 10^4$ | 100 |
| RON Substance | 10 | 4.4 | 147 | 6.1 | 235 |
| | 30 | 7.5 | 250 | 8.7 | 335 |
| | 100 | 6.8 | 227 | 8.2 | 315 |

It can be seen from the results shown in the Table III that the administration of the RON substance in a dose of 10 to 100 mg/kg greatly enhanced the antibody-producing ability in mice.

(c) Delayed Type Hypersensitivity Reaction (DHR)

This method is used to examine the effect of a substance to enhance the action of cell-mediated immunity due to the activation of T cells of the host amongst the immunomodulating actions.

The RON substance dissolved in a saline was administered orally to a test group of six 8-week-old ICR-CRJ mice (female; average weight: 27 g) for 8 consecutive days. For the control group, on the other hand, only a saline was administered in the same manner. At the fourth day from the administration, a 5% ethanol solution of picryl chloride was coated on the abdominal region which had been shaved to achieve a primary sensitization. At the eleventh day, a 1% olive oil solution of picryl was coated on the obverse and reverse side of the each ear of the mouse to accomplish a secondary sensitization. After 24 hours, an increase in the thickness of the ears was measured with a thickness gauge; that is, the increase in the thickness of the ear was determined by measuring the difference in thickness between before coating and after coating. On the other hand, in the case of tumor-bearing mice, Sarcoma-180 were transplanted intraperitoneally ($1 \times 10^5$ cells/mouse) prior to the administration of the RON substance and, thereafter, the same procedure as above was repeated.

The results are shown in the Table IV.

TABLE IV

| Sample | Dose (mg/kg) | Normal Mice Increase in Ear Thickness ($\mu$m) | Normal Mice Relative Value (%) | Tumor-bearing Mice Increase in Ear Thickness ($\mu$m) | Tumor-bearing Mice Relative Value (%) |
|---|---|---|---|---|---|
| Control (Saline) | — | 31.5 | 100 | 10.0 | 100 |
| RON Substance | 30 | 73.1 | 232 | 25.0 | 250 |
| | 100 | 69.3 | 220 | 24.3 | 243 |
| | 500 | 57.3 | 182 | 21.8 | 218 |

It can be seen from the results shown in the Table IV that the RON substance administered orally in a dose of 30 to 500 mg/kg enhanced greatly the cell-mediated immunity in the case of both normal and tumor-bearing mice.

After the RON was administered orally for a certain period to tumor bearing rats, number of T cells in peripheral blood, mesenteric lymph node, and spleen increased significantly by the administration of the RON. Concerning about the subset of T cells, helper T cells increased and suppressor T cells decreased. This fact also supports that the RON enhanced the T cell system.

From the results of the above-described tests (a), (b) and (c), it can be seen that the RON substance enhances greatly various immunity actions in mice and rats having different mechanisms. The immunomodulating agent can be used in cases in which the immunity function falls down or the recognizing function against the foreign antigen is poor. Thus the RON substance is expected to find uses as, for example, a therapeutic agent or an adjuvant therapeutic agent or a preventing agent or an agent for acceleration of recuperation after operation for infectious diseases and malignant tumors.

In addition to the above-described immunity activating or recovering capability, the immunomodulating agent may be used sometimes to normalize the abnormally stimulated immunity reaction; for example, may be applied to self immunity diseases such as rheumatism, collagen diseases, and allergy.

(3) Host Defense Activity

It is well known that the host defense activities of living body against the bacterial infectious diseases are based on the following principles: one is so-called the humoral immunity depending on the production of antibody against the invaded bacteria and another is so-called the cell-mediated immunity in which macrophage and T cell fight against the invaded bacteria. In general, the living body has a sufficient host defense activities against the invasion of such foreign bacteria. However, it is well known that in the tumor-bearing condition, particularly in the later stage of cancer, those activities fall down seriously, therefore, that the serious damage is caused even by some non-pathogenic bacteria usually living together in the host.

In order to determine if the RON substance enhances the mice host defense activities of the host against infectious diseases due to such bacteria, the inhibitory activity of the RON substance against the infection of *Escherichia coli*, a typical infectious microorganism against which is said the humoral immunity might participate, and against the infection of *Listeria monocytogenes*, which is said the cell-mediated immunity might participate, are examined.

Seven-week-old ICR-CRJ mice (female; average weight: 26 g) were divided into four groups of 20 mice each. The RON substance dissolved in a saline was injected subcutaneously in the back of the mice in a dose of 10, 30 or 100 mg/kg, at one day before and one day after the infection. For the control group, only a saline was injected in the same manner. Then, in the case of *E. coli*, $2 \times 10^7$ cells/mouse were infected subcutaneously in the back, and in the case of *L. monocytogenes*, $2 \times 10^7$ cells/mouse were infected intraperitoneally. After one week, the number of survival was compared. The protective effect was calculated by the following equation:

$$\text{Protective Effect (\%)} = \frac{\text{Number of survival in test group} - \text{Number of survival in control group}}{\text{Number of mice in one group}} \times 100$$

The results are shown in the Table V.

TABLE V

| Bacteria | Sample | Dose (mg/kg) | Administration Time | | | |
|---|---|---|---|---|---|---|
| | | | One Day Before Infection | | One Day After Infection | |
| | | | No. of Survival | Protective Effect (%) | No. of Survival | Protective Effect (%) |
| *E. coli* SB-001 | Control (Saline) | — | 0 | — | 0 | — |
| | RON Substance | 10 | 16 | 80 | 12 | 60 |
| | | 30 | 17 | 85 | 14 | 70 |
| | | 100 | 19 | 95 | 13 | 65 |
| *L. monocytogenes* SB-010 | Control (Saline) | — | 0 | — | 0 | — |
| | RON Substance | 10 | 8 | 40 | 8 | 40 |
| | | 30 | 14 | 70 | 12 | 60 |
| | | 100 | 12 | 60 | 10 | 50 |

It can be seen from the results shown in the Table V that the administration of the RON substance in a dose of 10 to 100 mg/kg prior to infection generates very strong host defense activities against the infection of *E. coli* and also significant activities against that of *L. monocytogenes*. Further, significant effects were observed in case of the administration of the RON substance after the infection.

In view of the fact that the RON substance is of no toxicity, this substance is expected to be a very useful host defense agent against infectious disease.

(4) Inducing Activity Of Tumor Necrosis Factor

Female, 8-week-old, ICR/CRJ mice were injected intravenously with 3 mg/mouse of Zymosan A (Sigma Co.) as a priming agent. At 7 days after the priming, 750 μg/mouse of the RON, or 25 μg/mouse of LPS (Difco Co., derived from *E. coli*) as a positive control, was injected intravenously to these mice as a eliciting agent. At 90 minutes after the eliciting, blood was collected from venous plexus of retro- orbit of the mice, centrifuged and sterilized by filtration to obtain activated serum. Thus the activated serum was submitted to the following tests.

(a) In Vitro Cytocidal Activity Against L-929 Cells

Cytocidal activity of the activated serum against L-929 cells was measured by the following procedures;

L-929 cells prelabelled with [$^3$H] thymidine (5 μCi/ml) were cultivated in the presence of the said serum for 24 hours at 37° C. in a $CO_2$ incubator. Released [$^3$H] from the cells was measured with liquid scintillation counter.

Eagle's MEM medium with 10% of fetal calf serum was used for cultivation and for dilution of the activated serum.

The results are shown in Table VI.

TABLE VI

| Eliciting agent | Dose (μg/mouse) | Cytocidal activity* (dilution fold of serum) |
|---|---|---|
| LPS | 25 | 210 |
| " | " | 220 |
| " | " | 200 |
| RON | 750 | 210 |
| " | " | 210 |
| " | " | 180 |

*Cytocidal activity is indicated by the dilution fold of the serum which gives 30% death of the target cells.

The table shows that the RON induced cytotoxic factor as strong as LPS which was used as a positive control, when mice were primed with Zymosan A and elicited with the RON substance.

(b) Necrotizing Activity Against Meth-A Solid Tumor

To confirm that the cytocidal activity mentioned above was due to the tumor necrosis factor, in vivo test was performed. Meth-A cells of $5 \times 10^5$ cells/mouse were inoculated subcutaneously in 8-week-old female BALB/C-CRJ mice. Seven days after the inoculation, 10 mice that had tumors reaching 7 mm in diameter with no spontaneous necrosis were selected and divided into 2 groups.

Tumor bearing mice in each group were injected intravenously with 0.5 ml/mouse of the serum with or without activation, and the changes appearing in the tumors were observed.

Although no changes were observed in 5 mice of the control group, distinct hemorrhagic necrosis was observed in all 5 mice of the test group received the activated serum.

(c) Endogenous Induction Of Tumor Necrosis Factor In Tumor Bearing Mice

Meth-A cells of $5 \times 10^5$ cells/mouse were inoculated subcutaneously in 10 female mice of 8-week-old BALB/C-CRJ. Two weeks after the inoculation, Zymosan, A of 3 mg/mouse was injected intravenously in the test group of 5 mice and 1 mg/mouse of the RON was injected intravenously one week after Zymosan A injection.

Although no changes were observed and tumors grew steadily in 5 mice of the control group, distinct hemorrhagic necrosis within one week after the injection of the RON was observed and growth of tumors was suppressed in all 5 mice of the test group.

From the results shown in (a), (b) and (c), it might be concluded that the RON has a strong inducing activity of tumor necrosis factor in mice and also has an activity inducing endogenous tumor necrosis factor in tumor bearing mice when used with a suitable priming agent. Therefore its anti tumor activity might be expected.

Because only such a toxic inducer of tumor necrosis factor as LPS has been known, it has not been possible to develop a useful way of utilization as a drug. But if such a non-toxic substance like the RON has an activity of inducing tumor necrosis factor, it might be very useful.

On the other hand, the following in vitro biological activities of the RON were confirmed as evidences to support such in vivo biological activities as mentioned above; when natural killer (NK) cells derived from mouse spleen were cultivated with YAC-1 cells (target cells) in the presence of the RON substance, cytocidal activity of NK cells against target cells was enhanced significantly by the RON; cytocidal activity of resident peritoneal macrophage against L-929 cells was enhanced significantly in the presence of the RON; secretion of interleukins or prostaglandins was enhanced in the presence of the RON substance.

The acute toxicity of the RON substance will hereinafter be described in detail.

Ten 5-week-old SD-CRJ rats (male; weight: 120-150 g) were used in the control and test group respectively. The RON substance was administered orally once at the physically maximum dose of 15 g/kg in the test group, and only a saline in the control group. No rat died. The increase of body weight in the test group was equal to that in the control group. Furthermore, no abnormality was observed in both appearance and necropsy. Thus it is considered that the $LD_5$ of this substance is larger than 15 g/kg and the substance has no acute toxicity.

In accordance with the present invention, the polysaccharide RON substance exhibiting superior antitumor and, immunomodulating activities in mice, host defense activity in mice against infectious microorganisms inducing activity in mice of tumor necrosis factor as described above can be obtained in a large amount, as demonstrated in Examples described hereinafter, by a combination of relatively easy procedures. Thus the present invention has a high practical value in the field of the commercial production of a polysaccharide having excellent biological activities from rice bran.

Furthermore, since the RON substance of the present invention is observed to have an interferon-inducing ability, it is expected to have activity in preventing or treating against virus diseases such as herpes and influenza.

Since the RON substance can be administered both orally and non-orally, it is expected to be a very useful antitumor (against transplantable tumors), immunomodulating, infectious disease-preventing or treating, or tumor necrosis factor inducing agent.

In the practical form of the drug, the RON substance can be produced singly or in combination with adjuvants (e.g., water, saline, polyethylene glycol, glycerogelatin, starch, dextrin, lactose, etc.) in the form of, e.g., liquid medicine, pellet, tablet, powder, suppository, etc.

The present invention is described in detail with reference to the following examples.

EXAMPLE 1

Tap water (125 liters) was added to 25 kg of commercially available rice bran which had been separated from pulverized rice and so forth by passing through a screen. The mixture was extracted at 120° C. for 1 hour and at 100° C. for 5 hours with constant stirring.

The extract was then filtered. The filtrate was concentrated under a reduced pressure to 40 liters The thusconcentrated filtrate was adjusted to pH 6.7 with sodium hydroxide and, thereafter, 500 mg of an α-amylase (produced by Nagase Sangyo Co., Ltd.) was added and an enzyme treatment was performed at 70° C. for 1 hour. After the enzyme treatment, the enzyme was inactivated by heating up to 100° C., and insolubles were removed by centrifugation. Ethanol was added to the final concentration of 30% (v/v). The precipitate formed was separated. This precipitate was dissolved again in water to remove insolubles. The soluble part was lyophilized and 508 g of a light yellow powder was obtained. Four grams of the said powder was dissolved again in ion-exchanged water, and insolubles were removed by centrifugation. The soluble part was applied on a gel filtration of Sepharose CL-6B (produced by Pharmacia Chemicals AB), and fractions eluted in the void volume were collected. This fractions were again applied on a column of DEAE-Sepharose CL-6B, and the fractions passed through the column without adsorption were collected, concentrated and thereafter lyophilized to obtain 500 mg of a white powder.

EXAMPLE 2

Commercially available rice bran (25 kg) was defatted by refluxing with 100 liters of hexane and then dried. The defatted rice bran was then treated in the same manner as in Example 1 to obtain 450 g of a light yellow powder. Four grams of the said powder was treated in the same manner as in Example 1 to obtain 550 mg of a white powder.

EXAMPLE 3

Commercially available defatted rice bran (3 kg) was mixed with 20 liters of water, and the mixture was then extracted at 120° C. for 2 hours with constant stirring. The extract was concentrated under a reduced pressure to obtain 5 liters of a concentrated solution. Then, 0.3 g of a crystalline α-amylase (produced by Nagase Sangyo Co., Ltd.) was added to the solution, and it was maintained at 60° C. for 5 hours. Thereafter, the mixture was heated to 100° C. and was subjected to centrifugation to get 4.9 liters of a supernatant. To the supernatant ethanol was added to the final concentration of 40% (v/v). The precipitate formed was separated and then lyophilized to obtain 88 g of a light yellow-brown powder.

Four grams of the said powder was treated in the same manner as in Example 1 to obtain 560 mg of a white powder.

EXAMPLE 4

Commercially available rice bran (20 kg) was passed through a 30-mesh screen to remove contaminants such as rice pieces, and then washed with 100 liters of ionexchanged water. Then, 50 liters of distilled water was added to the above-washed rice bran, and. the mixture was extracted at 110° C. for 3 hours with constant stirring. The extract was filtered. The filtrate was concentrated under a reduced pressure and centrifuged, whereupon 10 liters of a supernatant was obtained. Then, 250 mg of a crystalline α-amylase was added to it and kept at 65° C. for 24 hours. The mixture was heated to 100° C. Ethanol was then added to the final concentration of 30% (v/v). The precipitate formed was separated. This precipitate was dissolved again in 3 liters of water, and insolubles were removed, and concentrated again to 1 liter, and centrifuged to get a supernatant. This supernatant was dialyzed for 2 days with a running water and centrifuged to get 1 liter of a supernatant. To the supernatant 300 g of an anion exchanger, DEAE-Sepharose CL-6B, was added and stirred slowly for 1 hour at a room temperature, and centrifuged to get a supernatant. The supernatant was concentrated and lyophilized to obtain 150 g of a white powder.

EXAMPLE 5

Activated carbon (10 g) was added to 1 liter of a supernatant as obtained by dialysis and centrifugation in Example 4. After 30 minutes, the mixture was centrifuged. The thus obtained supernatant was subjected to the same ion-exchanging and lyophilizing treatment as in Example 4 to obtain 135 g of a white powder.

EXAMPLE 6

A 20 ml portion of 1 liter of a supernatant as obtained by dialysis and centrifugation in Example 4 was applied on a gel filtration using Sepharose CL-6B, and the void volume fractions were collected to make up 100 ml. This liquid was subjected to the same ion-exchanging and lyophilizing treatment as in Example 1 to obtain 2.0 g of a white powder.

EXAMPLE 7

The precipitate obtained by the ethanol precipitation after an α-amylase treatment in Example 1 was dissolved again in 10 liters of water. The solution was applied on an ultrafiltration to remove the low molecular part lower than 80,000 (molecular weight), and also to concentrate to 3 liters. The precipitate formed was removed by centrifugation, yielding 2.8 liters of a supernatant. This supernatant was subjected to the same ion-exchanging and lyophilizing treatment as in Example 1 to obtain 600 mg of a white powder.

EXAMPLE 8

To the solution subjected to the α-amylase treatment followed by the inactivation of the enzyme at 100° C. for 1 hour in Example 1 acetone was added to the final concentration of 40% (v/v). The precipitate formed was dissolved in 10 liters of water. Thereafter, the same procedure including the treatment using an ultrafilter as in Example 7 was applied to obtain 650 mg of a white powder.

EXAMPLE 9

To the solution subjected to the α-amylase treatment followed by the inactivation of the enzyme at 100° C. for 1 hour in Example 1 ammonium sulfate was added to the degree of saturation of 70% to achieve salting-out. The precipitate formed was collected by centrifugation, dissolved in 3 liters of water, and dialyzed against running water for 2 days. Trichloroacetic acid was added to the said solution to the concentration of 7%. The precipitate formed was removed by centrifugation. The thus obtained supernatant was dialyzed again against the running water for 2 days. The thus-obtained dialyzate was lyophilized to obtain 503 g of a light yellow powder. Four grams of the powder was dissolved in ion-exchanged water and then the same procedure including gel-filtrating, ion-exchanging and lyophilizing treatment as in Example 1 was applied to obtain 420 mg of a white powder.

EXAMPLE 10

The solution subjected to the α-amylase treatment in Example 1 was cooled to 40° C., and 600 mg of a proteinase (Pronase E, produced by Kaken Kagaku Co., Ltd.) was then added and was allowed to react for 24 hours. The reaction mixture was heated at 100° C. for 1 hour to inactivate the enzyme. Insolubles were removed by centrifugation. To the supernatant ethanol was added to the final concentration of 30% (v/v). The precipitate formed was collected by centrifugation and then dissolved in 10 liters of water. Thereafter, the same procedure including the treatment using an ultrafilter as in Example 7 was applied to obtain 550 mg of a white powder.

EXAMPLE 11

The supernatant solution (3 liters)obtained in the ultrafiltration conducted in the same manner as in Example 8, was admixed with an anion exchange resin, Amberlite IR-4B (500 g). The mixture was stirred for 1 hour at a room temperature, and filtered to remove the resin, thereby a supernatant solution (2.9 liters)was obtained This supernatant solution was concentrated and spray-dried, to obtain 350 g of a white powder.

EXAMPLE 12

To the water-soluble portion obtained by applying the ion-exchanging treatment in Example 11, ethanol was added to the final concentration of 40% (v/v). The precipitate formed was collected by centrifugation, washed and dehydrated three times with ethanol, and then dried in vacuo to obtain 300 g of a white powder.

EXAMPLE 13

To the white powder (2 g) obtained in Example 1, 2% aqueous sulfuric acid-formic acid solution (100 ml) was poured. The mixture solution was kept for 4 hours at 60° C. to hydrolyze the starting material. After completion of the hydrolysis, the reaction mixture was neutralized with barium carbonate and centrifuged to obtain a supernatant.

One-half of the supernatant thus obtained was subjected to a gel filtration on a column filled with Sepharose CL-2B, thereby a fraction $F_1$ having a molecular weight of about 20,000,000 or more which eluted in a void volume and a fraction $F_2$ having median molecular weight of about 1,000,000 were obtained.

Another one-half of the supernatant was subjected to a gel filtration on a column filled with Sephadex G-200, thereby a fraction $F_3$ having median molecular weight of about 100,000 and a fraction $F_4$ having median molecular weight of about 10,000 were obtained.

Each fraction was lyophilized and the fractions $F_1$, $F_2$, $F_3$ and $F_4$ gave white powder respectively in the following yield;

$F_1$: 400 mg, $F_2$: 250 mg, $F_3$: 300 mg, $F_4$: 250 mg.

Each fraction thus obtained was examined for biological activities according to the method described in the "detailed description of the invention". As apparent from the following results, each fraction exhibits biological activities comparable to the corresponding ones before hydrolysis. (1) Antitumor activity Activity against syngeneic tumor Meth-A was examined. Each fraction was administered orally at a dose of 30 mg/kg. The results are shown in the Table VII.

TABLE VII

| Fraction | Average tumor weight (g) | Degree of inhibition (%) |
|---|---|---|
| Control (Saline) | 7.50 | — |
| $F_1$ | 4.13 | 45 |
| $F_2$ | 3.75 | 50 |
| $F_3$ | 4.50 | 40 |
| $F_4$ | 4.95 | 34 |

(2) Immuno-Modulating Activity (a) Carbon Clearance Test (CCT)

Tumor-bearing mice were used. Each fraction was administered intraperitoneally at a dose of 30 mg/kg. The results are as shown in the Table VIII.

TABLE VIII

| Fraction | Phagocytic index | Relative value (to control) (%) |
|---|---|---|
| Control (Saline) | $108 \times 10^{-3}$ | 100 |
| $F_1$ | 151 | 140 |
| $F_2$ | 143 | 132 |
| $F_3$ | 135 | 125 |
| $F_4$ | 140 | 130 |

(b) Plaque Forming Cell Test (PFC)

Normal mice were used. Each fraction was administered intraperitoneally at a dose of 30 mg/kg. The mice thus treated were sentitized on 4th day of the test by injection of sheep red blood cells. The results are as shown in the Table IX.

TABLE IX

| Fraction | Plaque number/Spleen | Relative value (to control) (%) |
|---|---|---|
| Control (Saline) | $2.8 \times 10^4$ | 100 |
| $F_1$ | 6.6 | 236 |
| $F_2$ | 6.2 | 221 |
| $F_3$ | 5.9 | 211 |
| $F_4$ | 5.6 | 200 |

(c) Delayed Type Hypersensitivity Reaction (DHR)

Tumor-bearing mice were used. Each fraction was administered intraperitoneally at a dose of 30 mg/kg. The results are as shown in the Table X.

TABLE X

| Fraction | Increase in ear thickness (μm) | Relative value (to control) (%) |
|---|---|---|
| Control (Saline) | 11.0 | 100 |
| $F_1$ | 24.2 | 220 |
| $F_2$ | 26.4 | 240 |
| $F_3$ | 22.0 | 200 |
| $F_4$ | 21.3 | 194 |

(3) Host Defense Activity Against Infectious Diseases

Each fraction was administered subcutaneously at a dose of 30 mg/kg one day before the infection. The results are shown in Table XI.

TABLE XI

| | E. coli* | | L. monocytogenes** | |
|---|---|---|---|---|
| Fraction | Number of Survival | Protective Effect (%) | Number of Survival | Protective Effect (%) |
| Control (Saline) | 0 | — | 0 | — |
| $F_1$ | 19 | 95 | 11 | 55 |
| $F_2$ | 20 | 100 | 12 | 60 |
| $F_3$ | 18 | 90 | 9 | 45 |
| $F_4$ | 17 | 85 | 8 | 40 |

*E. coli: Escherichia coli SB-001
**L. monocytogenes: Listeria monocytogenes SB-010

Each fraction was administered subcutaneously at a dose of 30 mg/kg one day after the infection. The results are shown in Table XII.

TABLE XII

| | E. coli | | L. monocytogenes | |
|---|---|---|---|---|
| Fraction | Number of Survival | Protective Effect (%) | Number of Survival | Protective Effect (%) |
| Control (Saline) | 0 | — | 0 | — |
| $F_1$ | 15 | 75 | 10 | 50 |
| $F_2$ | 16 | 80 | 11 | 55 |
| $F_3$ | 14 | 70 | 8 | 40 |
| $F_4$ | 13 | 65 | 7 | 35 |

(4) Inducing Activity Of Tumor Necrosis Factor (a) In Vitro Cytocidal Activity Against L-929 Cells Cytocidal activity of the serum against L-929 cells when 750 μg/mouse of the RON was injected intravenously as an elicitor is shown in the following table. As a positive control, 25 μg, mouse of LPS was injected in the same route.

TABLE XIII

| Fraction | Cytocidal activity (dilution fold of serum) |
|---|---|
| LPS (positive control) | 200 |
| $F_1$ | 170 |
| $F_2$ | 200 |
| $F_3$ | 150 |
| $F_4$ | 135 |

(b) Necrotizing Activity Against Meth-A Solid Tumor

Hemorrhagic necrosis was observed in all tumor bearing mice injected with the activated serum prepared in (a).

(c) Endogenous Induction Of Tumor Necrosis Factor In Tumor Bearing Mice

When 1 mg/mouse of each fraction of the RON was injected intravenously one week after the injection of 3 mg/mouse of Zymosan A in Meth-A bearing mice, distinct hemorrhagic necrosis was observed and growth of tumors was suppressed in all mice of test group within one week after injection of each fraction.

What is claimed is:

1. A deproteinized polysaccharide RON substance containing glucose as the sole sugar constituent, and composed solely of linear α-1,6 glucoside linkage and is further characterized by:
   (a) having as a structural repetition unit(6 G) wherein G is α-D-glucopyranosyl group;
   (b) being incapable of passing through a dialysis membrane;
   (c) being insoluble in alcohol, acetone, hexane, benzene, ethyl acetate, carbon tetrachloride, chloroform and ether; soluble in water, formamide and dimethyl sulfoxide;
   (d) being neutral in a 9% aqueous solution;
   (e) exhibiting elementary analysis:
   C 40.4–42.4%, H 5.8–6.4%, ash 3.1–3.3%;
   (f) containing in a combined state a small amount of inorganic elements (Si, P, K, Na, Ca, Mg and Cl);
   (g) being positive in anthrone-sulfuric acid reaction, phenol-sulfuric acid reaction, chromotrope-sulfuric acid reaction; negative in biuret reaction, the Lowry-Folin reaction, the Elson-Morgan reaction and starch-iodine reaction.
   (h) exhibiting a specific rotation as $[\alpha]D^{20} = +142° - +145°$ (H2O);
   (i) having no definite melting point, turning brown at 220° C. and carbonizing at 280° C.;
   (j) showing ultraviolet absorption spectrum as shown in FIG. 1 of the attached drawings;
   (k) showing infrared absorption spectrum as shown in FIG. 2 of the attached drawings;
   (l) showing $^3$C-NMR spectrum as shown in FIG. 3 of the attached drawings.

2. A pharmacological composition effective in inhibiting the growth of transplantable tumors, having immunomodulating activity in mice and potentiating the host defense ability of mice against infectious microorganisms, and inducing the production of tumor necrosis factor in mice, comprising an effective amount of a deproteinized polysaccharide RON substance and a pharmaceutically acceptable vehicle, said polysaccharide RON substance containing glucose as the sole sugar constituent, and composed solely of linear α-1,6-glucoside linkage in the linear part of the saccharide and having a small amout of 3,6 branched structure and is further characterized by:
   (a) having as a structural repetition unit(6 G) wherein G is α-D-glucopyranosyl group;
   (b) being incapable of passing through a dialysis membrane;
   (c) being insoluble in alcohol, acetone, hexane, benzene, ethyl acetate, carbon tetrachloride, chloroform and ether; soluble in water, formamide and dimethyl sulfoxide;
   (d) being neutral in a 1% aqueous solution;
   (e) exhibiting elementary analysis:
   C 40.4–42.4%, H 5.8–6.4%, ash 3.1–3.3%;
   (f) containing in a combined state of a small amount of inorganic elements (Si, P, K, Na, Ca, Mg and Cl);
   (g) being positive in anthrone-sulfuric acid reaction, phenol-sulfuric acid reaction, chromotrope-sulfuric acid reaction, negative in biuret reaction, the Lowry-Folin reaction, the Elson-Morgan reaction and starch-iodine, reaction;
   (h) exhibiting a specific rotation as $[\alpha]D^{20} = +142° - 145°$ (H$_2$O);
   (i) having no definite melting point, turning brown at 220° C. and carbonizing at 280° C.;
   (j) showing ultraviolet absorption spectrum as shown in FIG. 1 of the attached drawings;
   (k) showing infrared absorption spectrum as shown in FIG. 2 of the attached drawings;
   (l) showing $^{13}$C-NMR spectrum as shown in FIG. 3 of the attached drawings.

* * * * *

UNITED STATES PATENT AND TRADEMARK OFFICE
CERTIFICATE OF CORRECTION

PATENT NO.  : 4,762,825
DATED       : August 9, 1988
INVENTOR(S) : TAKEO et al

It is certified that error appears in the above-identified patent and that said Letters Patent is hereby corrected as shown below:

Column 17 (claim 1), line 23, "in a9%" should read

--in a 1%--.

Column 18 (claim 2), line 12, "amout" should read --amount--.

Signed and Sealed this

Thirty-first Day of December, 1991

Attest:

HARRY F. MANBECK, JR.

Attesting Officer

Commissioner of Patents and Trademarks